United States Patent [19]

Hommeltoft

[11] Patent Number: 5,472,921

[45] Date of Patent: Dec. 5, 1995

[54] PROCESS FOR THE RECOVERY OF SPENT FLUORINATED SULPHONIC ACID CATALYST IN AN ALKYLATION PROCESS

[75] Inventor: Sven I. Hommeltoft, Hillerod, Denmark

[73] Assignee: Haldor Topsøe A/S, Denmark

[21] Appl. No.: 229,686

[22] Filed: Apr. 19, 1994

[30] Foreign Application Priority Data

Apr. 20, 1993 [DK] Denmark ................................. 0440/93

[51] Int. Cl.⁶ .................................................. B01J 20/34
[52] U.S. Cl. ............................ 502/31; 502/33; 502/216; 502/224; 585/458
[58] Field of Search ............................... 502/20, 150, 31, 502/33, 216, 224; 585/458, 720, 721, 730

[56] References Cited

U.S. PATENT DOCUMENTS 4,317,949  3/1982  Vaughan .................................. 585/458
5,220,095  6/1993  Hommeltoft et al. ................ 502/20 X

*Primary Examiner*—Michael Lusignan
*Attorney, Agent, or Firm*—Ostrolenk, Faber, Gerb & Soffen

[57] ABSTRACT

Process for the recovery of fluorinated sulphonic acid catalyst from tar being formed during alkylation of hydrocarbons in the presence of the fluorinated sulphonic acid catalyst and containing spent fluorinated sulphonic acid catalyst in form of salts with basic components in the tar, which process comprises, treating the tar with an alkyl ester of sulphuric acid to form a fluorinated sulphonic acid alkyl ester;

separating the obtained ester from the tar by stripping the ester off the tar with an inert stripping agent; and finally recovering the separated sulphonic acid alkyl ester from the stripping agent.

8 Claims, No Drawings

PROCESS FOR THE RECOVERY OF SPENT FLUORINATED SULPHONIC ACID CATALYST IN AN ALKYLATION PROCESS

The present invention is directed to improvements in the alkylation of aliphatic hydrocarbons in the presence of a fluorinated sulphonic acid catalyst.

More particulary, the invention is related to the recovery of the fluorinated sulphonic acid from tar being formed as by-product during alkylation of hydrocarbons.

Acid catalyzed alkylation of aliphatic hydrocarbons with olefinic hydrocarbons is a well known process for the preparation of high octane gasoline products. Alkylation of aliphatic hydrocarbons is generally accomplished in the liquid phase by reacting paraffins and olefins in the presence of a strong acid catalyst.

Utilization of fluorinated sulphonic acids as efficient alkylation catalysts in the alkylation of aliphatic hydrocarbons with olefins, is disclosed in European Patent Application No. 433,954, which by reference is enclosed herein. By the disclosed process, a process stream including a hydrocarbon substrate and an olefinic alkylating agent is reacted in contact with a fluorinated sulphonic acid catalyst in a fixed bed alkylation reactor containing polar contact material. On the contact material is established a reaction zone with the fluorinated sulphonic acid catalyst adsorbed within a confined area of the contact material. In the reaction zone, the process stream is converted at alkylating conditions to a product stream of alkylated hydrocarbons by catalysis of the fluorinated sulphonic acid adsorbed on the contact material.

During the alkylation reaction, the acid catalyst and, consequently, the reaction zone moves as a well-defined band between the ends of the reactor due to interaction with the process stream flowing through and reacting in the zone.

During migration of the acid catalyst on the contact material, the catalytic activity of the fluorinated sulphonic acid is substantially retained and the acid is still catalytic active when the reaction zone reaches the reactor outlet.

Although it is possible to reuse the acid catalyst, as it reaches the outlet end of the alkylation reactor by reversing the flow direction of the process stream being introduced into the alkylation reactor, small amounts of the acid catalyst will continuously be trapped in tar by-product being formed by side reactions during the process. The tar adsorbs like the acid catalyst as a movable band on the support material adjacent to the reaction zone. It is, thus, possible to withdraw the tar from the reactor, whenever a tar band reaches one of the ends of the reactor.

Even if the tar contains only small amounts of spent acid catalyst, it is desirable to recover the catalyst from the tar in order to improve the economy of the alkylation process. Conventionally methods, like distillation or extraction of the acid directly from the tar, are not efficient because of strong interaction between sulphonic acid and basic components in the tar.

It is, therefore, a principal object of this invention to provide a process for the efficient recovery of fluorinated sulphonic acid catalyst from an alkylation process.

In my previous patent application DK 0287/93, I have disclosed a recovery process, at which spent fluorinated sulphonic acid catalyst is regained by stepwise treating tar from an alkylation process containing spent catalyst with a proton donating acid to convert the catalyst to its free acid form and then removing the acid by stripping the tar with an inert stripping agent.

The above process provides an efficient recovery of valuable fluorinated sulphonic acid catalyst. In order to obtain high recovery rates the process has, however, to be carried out at low pressure.

It is, thus, the general object of this invention, to improve the known processes for the recovery of spent acid catalyst from alkylation of hydrocarbons and to provide a process allowing recovery of the catalyst from alkylation tar at higher pressure than in the known process.

Accordingly, a broad embodiment of the invention is directed towards a process for the recovery of fluorinated sulphonic acid catalyst from tar being formed during alkylation of hydrocarbons in the presence of the fluorinated sulphonic acid catalyst and containing spent fluorinated sulphonic acid catalyst in form of salts with basic components in the tar, which process comprises, treating the tar with an alkyl ester of sulphuric acid to form a fluorinated sulphonic acid alkyl ester;

separating the obtained ester from the tar by stripping the ester off the tar with an inert stripping agent; and finally recovering the separated sulphuric acid alkyl ester from the stripping agent.

Addition of sulphuric acid alkyl esters to the tar results in esterification of the spent acid catalyst, which is present predominantly as salt formed with basic compounds contained in the tar. Upon addition of a sulphuric acid ester, an equilibrium of transesterification with the spent catalyst is readily established.

The fluorinated sulphonic acid alkyl esters thereby obtained are more volatile compounds than their free acid derivates, and easier to separate from the tar.

Volatility of the formed esters decreases with increasing molecular weight in the alkyl group. It is, therefore, preferred to employ sulphuric acid esters with lower alkyl groups, most preferably propyl and butyl groups.

In order to push the equilibrium of the esterification reaction in favour of formation of fluorinated sulphonic acid alkyl esters, the esters are removed continuously as they are formed in the tar by action of the inert stripping agent.

Suitable stripping agents comprise any compound which is inert with respect to the components and acids being present in the mixture.

Presently, the most preferred stripping agent is selected from the group of $C_{10}$–$C_{14}$ aliphatic hydrocarbons.

Acid recovery may further be increased through addition of oleum, i.e. a mixture of sulphuric acid with sulphuric trioxide, to the tar in an amount of 0.1 to 50 vol %.

In operating the process industrially, stripping of the tar will be carried out in a stripping column equipped with valve trays or filler bodies. The tar mixed with alkyl sulphate is continuously introduced at the top of the column and is withdrawn from the bottom. The stripping agent is introduced in the bottom of the column and flows in gaseous form upwardly and countercurrently with the tar alkyl sulphate mixture towards the top of the column. During passage through the column, the stripping agent comes into intimate contact with the mixture and the fluorinated sulphonic acid ester being at the stripping conditions used in the column in the vapour phase, is stripped off from the tar ester mixture by vapours of the stripping agent. Stripped off fluorinated sulphonic acid ester is withdrawn at the top of the column together with the stripping agent. The fluorinated sulphonic acid ester is finally separated from the stripping agent by conventional separation techniques, comprising phase separation, condensation, distillation, adsorption and the like. The ester may be recycled without any further treatment to the alkylation process.

EXAMPLE 1

20 ml (25.5 g) tar containing 13.7 g $CF_3SO_3H$ from the alkylation of isobutane in the presence of trifluoromethane sulphonic acid catalyst ($CF_3SO_3H$) were added to a 100 ml flask and mixed with 30 ml (33.5 g) diisopropyl sulphate and 45 ml n-decane stripping agent. The mixture was kept at 30°–40° C. and a pressure of 6 mbar, at which conditions esterification of the acid and stripping of the formed ester were carried out simultaneously. A vapour phase collected from a 300 ml stripping column with 6 mm Raschig-rings connected to the flask, was separated into a phase containing isopropyl trifluoromethane sulphonate and a lighter phase of n-decane stripping agent.

After 100 min. 10.8 g $CF_3SO_3H$ were recovered as isopropyl ester. The residual 2.9 g of the acid were retained in the tar.

EXAMPLE 2

20 ml tar containing 15.4 g $CF_3SO_3H$ were mixed with 50 ml n-decane, 20 ml diisopropyl sulphate and 1.8 ml 65% oleum. The mixture was treated in the same way as in Example 1, which provided 92% recovery of $CF_3SO_3H$.

I claim:

1. Process for the recovery of fluorinated sulphonic acid catalyst from tar being formed during alkylation of hydrocarbons in the presence of the fluorinated sulphonic acid catalyst and containing spent fluorinated sulphonic acid catalyst in form of salts with basic components in the tar, which process comprises, treating the tar with an alkyl ester of sulphuric acid to form a fluorinated sulphonic acid alkyl ester;

separating the obtained ester from the tar by stripping the ester off the tar with an inert stripping agent; and finally recovering the separated sulphonic acid alkyl ester from the stripping agent.

2. The process of claim 1, wherein the alkyl ester of sulphuric acid for treatment of the tar comprises sulphuric acid propyl and/or butyl ester.

3. The process of claim 1, wherein the stripping agent is selected from the group of $C_{10}$–$C_{14}$ aliphatic hydrocarbons.

4. The process of claim 1, wherein oleum in an amount of between 0.1 and 50% by volume in addition to the sulphuric acid alkyl ester is added to the tar.

5. The process of claim 1, wherein the separation of the spent fluorinated sulphonic acid catalyst from the tar sulphuric acid alkyl ester mixture is carried out continuously in a stripping column with the mixture passing in countercurrent flow with the stripping agent through the column.

6. The process of claim 2, wherein the separation of the spent fluorinated sulphonic acid catalyst from the tar sulphuric acid alkyl ester mixture is carried out continuously in a stripping column with the mixture passing in countercurrent flow with the stripping agent through the column.

7. The process of claim 3, wherein the separation of the spent fluorinated sulphonic acid catalyst from the tar sulphuric acid alkyl ester mixture is carried out continuously in a stripping column with the mixture passing in countercurrent flow with the stripping agent through the column.

8. The process of claim 4, wherein the separation of the spent fluorinated sulphonic acid catalyst from the tar sulphuric acid alkyl ester mixture is carried out continuously in a stripping column with the mixture passing in countercurrent flow with the stripping agent through the column.

* * * * *